United States Patent
Becker et al.

(10) Patent No.: US 6,319,243 B1
(45) Date of Patent: *Nov. 20, 2001

(54) CONTAINERS AND METHODS FOR STORING AND ADMIXING MEDICAL SOLUTIONS

(75) Inventors: Michael Becker, Palatine; Michael Masterson, Gurnee, both of IL (US); Freddy Desbrosses, Thuin (BE)

(73) Assignee: Baxter International, Inc., Deerfield, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/015,475

(22) Filed: Jan. 29, 1998

Related U.S. Application Data

(62) Division of application No. 08/712,174, filed on Sep. 11, 1996, now abandoned.

(51) Int. Cl.[7] .................... A61M 31/00; B65D 81/02
(52) U.S. Cl. .................... 604/518; 604/520; 604/500; 604/410; 604/87; 206/221; 206/568
(58) Field of Search ............... 604/87–91, 49, 604/409–410, 500, 518, 520, 522, 403, 408; 206/219, 221, 222, 568

(56) References Cited

U.S. PATENT DOCUMENTS

| | | |
|---|---|---|
| 2,882,692 | 4/1959 | Robbins . |
| 2,898,744 | 8/1959 | Robbins . |
| 3,036,894 | 5/1962 | Forestiere . |
| 3,074,544 | 1/1963 | Bollmeier et al. . |
| 3,478,871 | 11/1969 | Sager . |
| 3,722,833 | 3/1973 | Inoue et al. . |
| 3,749,620 | 7/1973 | Montgomery . |
| 3,804,077 | 4/1974 | Williams . |
| 3,830,475 | 8/1974 | Inoue et al. . |
| 3,847,279 | 11/1974 | Montgomery . |
| 3,940,905 | 3/1976 | Perry, 3rd . |
| 3,964,604 | 6/1976 | Prenntzell . |
| 3,983,994 | 10/1976 | Wyslotsky . |
| 4,110,303 | 8/1978 | Gergen et al. . |
| 4,294,247 | 10/1981 | Carter et al. . |
| 4,340,049 | 7/1982 | Munsch . |
| 4,362,242 | 12/1982 | Cheetham . |
| 4,386,622 | 6/1983 | Munsch . |

(List continued on next page.)

FOREIGN PATENT DOCUMENTS

| | | |
|---|---|---|
| 1 227 382 | 10/1966 | (DE) . |
| 44 10 875 | 10/1995 | (DE) . |
| 0875231A2 | * 11/1998 | (DE) . |

(List continued on next page.)

OTHER PUBLICATIONS

Black et al., "A Study of Intravenous Emulsion Compatibility: Effects of Dextrose, Amino Acids, and Selected Electrolytes", *Drug Intelligence and Clinical Pharmacy*, vol. 15, 1981, pp. 184–193.

(List continued on next page.)

*Primary Examiner*—Angela D. Sykes
*Assistant Examiner*—Patricia Bianco
(74) *Attorney, Agent, or Firm*—Jeffrey C. Nichols; Mark J. Buonaiuto; Francis C. Kowalik

(57) ABSTRACT

Containers and methods for storing medical solutions are provided. More specifically, containers and methods for storing components that are to be admixed together to create a final solution, one of the components comprising a lipid. In an embodiment, a container including an interior defining at least two chambers. The first chamber includes a lipid containing liquid. The second chamber includes a liquid that does not include a lipid. The first and second chambers are separated by an openable seal.

6 Claims, 3 Drawing Sheets

U.S. PATENT DOCUMENTS

| | | |
|---|---|---|
| 4,396,383 | 8/1983 | Hart . |
| 4,402,402 | 9/1983 | Pike . |
| 4,410,321 | 10/1983 | Pearson et al. . |
| 4,411,662 | 10/1983 | Pearson . |
| 4,429,076 | 1/1984 | Saito et al. . |
| 4,432,755 | 2/1984 | Pearson . |
| 4,458,811 * | 7/1984 | Wilkinson ............................. 206/219 |
| 4,465,488 | 8/1984 | Richmond et al. . |
| 4,467,588 | 8/1984 | Carveth . |
| 4,476,976 | 10/1984 | Smith . |
| 4,496,046 | 1/1985 | Stone et al. . |
| 4,507,114 | 3/1985 | Bohman et al. . |
| 4,519,499 | 5/1985 | Stone et al. . |
| 4,534,509 | 8/1985 | Holzner . |
| 4,537,303 | 8/1985 | Muhlbauer . |
| 4,540,089 | 9/1985 | Maloney . |
| 4,548,606 | 10/1985 | Larkin . |
| 4,556,325 | 12/1985 | Katzin . |
| 4,557,377 | 12/1985 | Maloney . |
| 4,568,723 | 2/1986 | Lu . |
| 4,583,971 | 4/1986 | Bocquet et al. . |
| 4,602,910 | 7/1986 | Larkin . |
| 4,608,043 | 8/1986 | Larkin . |
| 4,610,684 | 9/1986 | Knox et al. . |
| 4,629,080 | 12/1986 | Carveth . |
| 4,630,727 | 12/1986 | Feriani et al. . |
| 4,637,199 | 1/1987 | Steck et al. . |
| 4,643,926 | 2/1987 | Mueller . |
| 4,675,020 | 6/1987 | McPhee . |
| 4,686,125 | 8/1987 | Johnston et al. . |
| 4,726,997 | 2/1988 | Mueller et al. . |
| 4,764,404 | 8/1988 | Genske et al. . |
| 4,769,261 | 9/1988 | Hazelton et al. . |
| 4,770,295 | 9/1988 | Carveth et al. . |
| 4,778,697 | 10/1988 | Genske et al. . |
| 4,781,679 | 11/1988 | Larkin . |
| 4,786,279 | 11/1988 | Wilkinson et al. . |
| 4,795,782 | 1/1989 | Lutz et al. . |
| 4,803,102 | 2/1989 | Raniere et al. . |
| 4,816,343 | 3/1989 | Mueller et al. . |
| 4,936,841 | 6/1990 | Aoki et al. . |
| 4,937,139 | 6/1990 | Genske et al. . |
| 4,961,495 | 10/1990 | Yoshida et al. . |
| 4,966,795 | 10/1990 | Genske et al. . |
| 4,997,083 * | 3/1991 | Loretti et al. ........................ 206/219 |
| 5,070,143 | 12/1991 | Pucci et al. . |
| 5,071,686 | 12/1991 | Genske et al. . |
| 5,132,149 | 7/1992 | Kotani et al. . |
| 5,133,172 | 7/1992 | Soubrier . |
| 5,139,831 | 8/1992 | Mueller . |
| 5,176,634 | 1/1993 | Smith et al. . |
| 5,196,001 | 3/1993 | Kao . |
| 5,209,347 * | 5/1993 | Fabisiewicz et al. ................ 206/219 |
| 5,252,222 * | 10/1993 | Matkovich et al. ................. 210/650 |
| 5,257,985 * | 11/1993 | Puhl ..................................... 604/410 |
| 5,278,149 * | 1/1994 | Provost et al. ........................ 514/23 |
| 5,316,826 | 5/1994 | Kotani et al. . |
| 5,317,059 | 5/1994 | Chundury et al. . |
| 5,352,191 | 10/1994 | Sunago et al. . |
| 5,356,709 | 10/1994 | Woo et al. . |
| 5,380,315 | 1/1995 | Isono et al. . |
| 5,397,303 | 3/1995 | Sancoff et al. . |
| 5,423,421 | 6/1995 | Inoue et al. . |
| 5,425,447 | 6/1995 | Farina . |
| 5,462,526 | 10/1995 | Barney et al. . |
| 5,484,431 | 1/1996 | Scharf et al. . |
| 5,493,774 | 2/1996 | Grabenkort . |
| 5,501,887 | 3/1996 | Tanaka et al. . |
| 5,509,898 | 4/1996 | Isono et al. . |
| 5,577,369 * | 11/1996 | Becker et al. ........................ 53/474 |
| 5,695,840 | 12/1997 | Mueller . |
| 5,697,407 * | 12/1997 | Lasonde ............................... 141/104 |
| 5,706,937 | 1/1998 | Futagawa et al. . |
| 5,728,681 * | 3/1998 | Kido ...................................... 514/23 |
| 5,770,051 | 6/1998 | Joie et al. . |
| 5,853,388 * | 12/1998 | Semel ................................... 604/82 |
| 5,981,523 * | 11/1999 | Panetta et al. . |
| 6,007,529 * | 12/1999 | Gustafson et al. ................... 604/410 |
| 6,024,220 * | 2/2000 | Smith et al. . |
| 6,074,366 * | 6/2000 | Rogers et al. . |
| 6,083,584 * | 7/2000 | Smith et al. . |

FOREIGN PATENT DOCUMENTS

| | | |
|---|---|---|
| 0 122 968 | 10/1984 | (EP) . |
| 0 596 497 | 5/1994 | (EP) . |
| 0 704 199 | 4/1996 | (EP) . |
| 1 115 593 | 3/1957 | (FR) . |
| 2 423 413 | 11/1979 | (FR) . |
| 2 570 279 | 3/1986 | (FR) . |
| 936706 | 9/1963 | (GB) . |
| 1290422 | 9/1972 | (GB) . |
| 1328539 | 8/1973 | (GB) . |
| 1393114 | 5/1975 | (GB) . |
| 1562235 | 3/1980 | (GB) . |
| 2122166 | 1/1984 | (GB) . |
| 2134067 | 8/1984 | (GB) . |
| WO 81/03009 | 10/1981 | (WO) . |
| WO 82/02700 | 8/1982 | (WO) . |
| PCT/US82/ 00473 | 1/1983 | (WO) . |
| WO 92/02271 | 2/1992 | (WO) . |
| WO 95/26177 | 10/1995 | (WO) . |
| WO 97/05852 | 2/1997 | (WO) . |
| WO 97/37628 | 10/1997 | (WO) . |
| WO 97/39952 | 10/1997 | (WO) . |
| WO 97/42897 | 11/1997 | (WO) . |
| WO 98/16183 | 4/1998 | (WO) . |

OTHER PUBLICATIONS

Brown et al., "Total Nutrient Admixture: A Review", *Journal of Parenteral And Enteral Nutrition*, vol. 10, No. 6, 1986, pp. 650–658.

Washington et al., "The electrokinetic properties of phospholipid stabilized fat emulsions. IV. The effect of glucose and of pH", *International Journal of Pharmaceutics*, vol. 64, 1990, pp. 217–222.

Wells, "The Effect of Nutrient Additives on Total Nutrient Admixture Stability", *A Guide to Total Nutrient Admixtures*, Precept Press, Inc., 1992, pp. 21–22.

"Nutriflex—Prefilled TPN Double–Chamber Bag," brochure by Braun, 1995, 6 pages.

"We Make Medical Products Safe Along Their Way," brochure by Kobusch/Sengewald, pp. 1–12.

"Propyflex Fluid Bags—Our Solution For Your Solutions," brochure by Kobusch/Sengewald, 4 pages.

Derwent Patent Abstract for EP 538569.

U.S.O.G. Abstract for U.S. Patent No. 5,217,433.

* cited by examiner

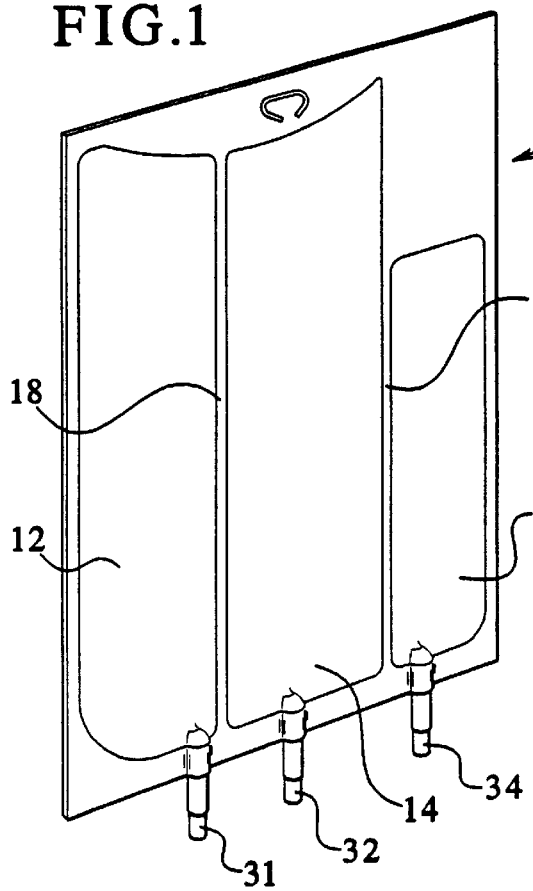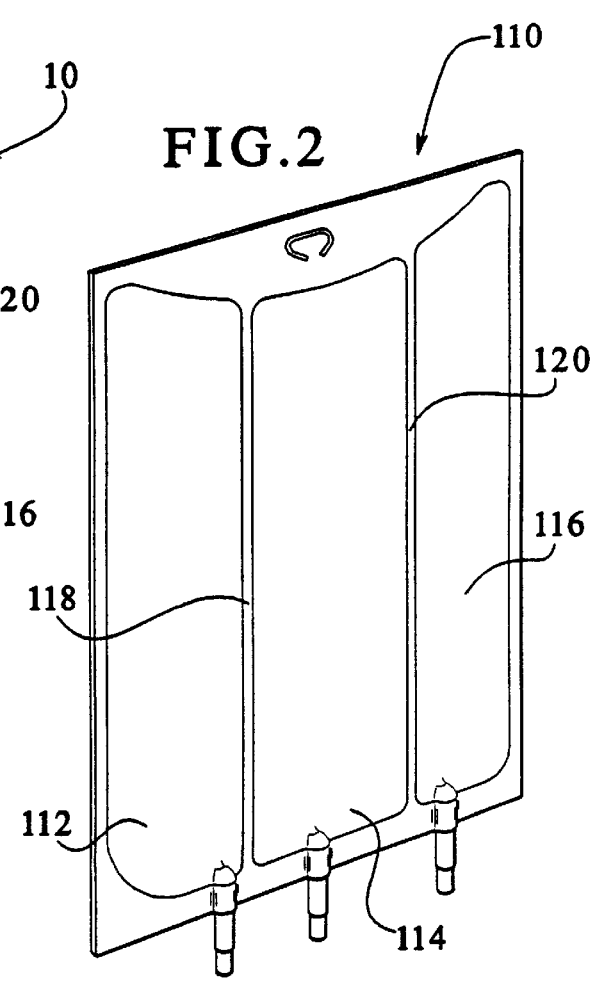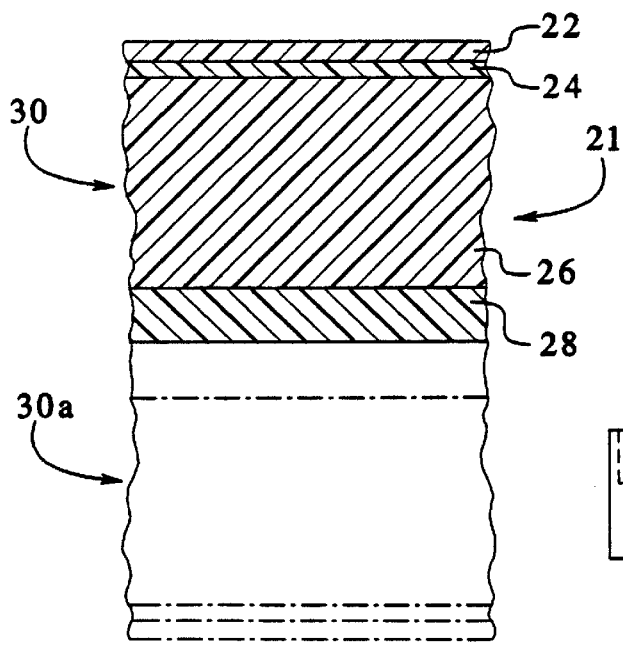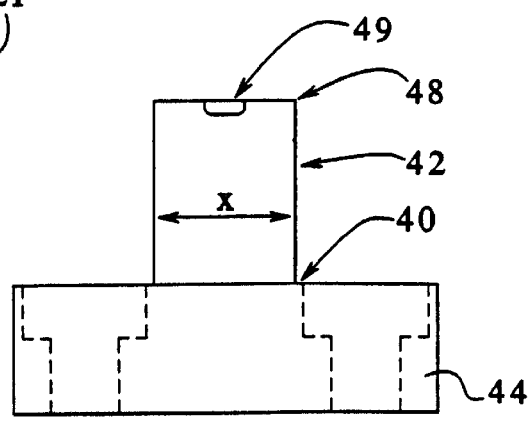

CONTAINERS AND METHODS FOR STORING AND ADMIXING MEDICAL SOLUTIONS

This is a Divisional patent application of U.S. Ser. No. 08/712,174 that was filed on Sep. 11, 1996 now abandoned.

BACKGROUND OF THE INVENTION

The present invention relates generally to medical products and procedures. More specifically the present invention relates to containers for storing medical solutions and methods of sterile admixing such solutions before they are administered to a patient.

It is of course known to store medical solutions in containers. A variety of such solutions are housed and stored in such containers. Such medical solutions can include, for example, parenteral, enteral, dialysis solutions, nutrients and pharmacologic agents, including gene therapy and chemotherapy agents.

These containers can be either constructed from glass or plastic. Plastic containers can either be rigid or flexible. Flexible containers are constructed from plastic films.

Although there are a great variety of solutions that are used in medical treatments today, there are however, a number of issues that can limit the ability to store at least certain medical solutions. For example, due to stability, compatibility or other concerns a number of medical solutions can not be premixed. Rather, the individual components must be stored separately. Typically these components are either stored in separate containers and admixed before use, or are stored in separate compartments of a flexible container and then mixed prior to use. For example, amino acids and dextrose solutions require storage in separate containers or compartments.

One of the disadvantages of storing components in separate containers and then mixing them together is that the mixing process can compromise sterility of the system and/or process. Additionally, such a mixing process creates a labor intensive process. Still further, it is possible for mistakes to occur during the admixing process due to the amount of solution to be added from the separate containers into the final container for the patient.

To deal with the disadvantages of separate containers, it is known to provide flexible containers that include multiple chambers. To this end, such containers have an interior that defines two or more chambers. One way to create such a container is with a heat seal that divides the interior into two chambers. Such containers are disclosed, for example, in U.S. Pat. Nos.: 4,396,488; 4,770,295; 3,950,158; 4,000,996; and 4,226,330.

It is also known to use frangible valves between the heat seal to allow for the selective communication and mixing of the two components stored in the separate chambers. See, for example, U.S. Pat. No. 4,396,488.

However, such a structure-frangible valves—may not be desirable for a number of reasons, including, inter alia, mixing time, particulate matter generation, difficulty in opening, difficulty in achieving a homogenous mixture, and cost. An alternative to frangible valves is disclosed in U.S. Pat. Nos.: 3,950,158; 4,000,996; and 4,226,330. In these patents multiple chamber containers are disclosed with a line of weakness, such as a score line, which breaks upon the application of pressure.

U.S. Pat. No. 4,770,295 discloses a selectively openable seal line positioned between two sheets of flexible thermoplastic material. The seal line is resistant to unintentional opening forces but opens upon the application of a specific force.

Additionally, it is known to use tear tabs or tear strips for plastic containers. See U.S. Pat. Nos.: 2,991,000; and 3,983,994. A disadvantage of these systems is they involve the use of relatively complicated seal structures.

A number of other issues must also be addressed in constructing containers for use in the medical industry. For example, it is typically necessary to sterilize the container and solution after manufacturing the container and solution. Typically the products are sterilized by steam sterilization or autoclaving. Autoclaving sterilization can alter the thermal properties of the film used to form the container as well as the seal between the chambers in the container. Still further heat sterilization can adversely effect the solutions contained therein unless they are maintained at certain conditions, an example of such a composition is dextrose.

Of course, it is necessary that the seal between any multiple chamber container is able to withstand external stresses. Such stresses can include pressure that may be applied to one or more of the chambers from, for example, squeezing thereof or accidentally dropping the bag. Therefore the seal must be sufficiently strong. But, on the other hand, the seal must not be too strong so that it is not possible to mix the solutions contained therein before one intends that they be mixed.

Still further, a problem that one faces, especially with respect to parenteral nutritional solutions, is that the components that comprise the solutions may not only not be compatible with each other but, also may not be compatible with the materials from which the container is constructed. For example, lipids cannot be housed in typical plastic materials used to make containers. Lipids can leach certain materials out of the plastic; if a lipid is housed in a polyvinyl chloride material it will leach out the plasticizers. Leaching of the plasticizer causes toxicity issues. Additionally, when the plasticizers are leached out, the plastic becomes rigid. Therefore, heretofore commercially available lipid products only have been housed in glass containers.

One form of potentially life supporting therapy is total parenteral nutrition or hyperalimentation. Typically, parenteral nutrition solutions that provide total nutritional requirements to a patient include a lipid component, a carbohydrate component, a protein component, and vitamins and minerals.

Because of a number of stability and related issues, total parenteral nutrition solutions can not be stored in a ready to use state. Thus, it is necessary to admix the solutions prior to use.

Heretofore, due to the inability to store all the base components that may be necessary for a parenteral nutritional solution in a single container, it is known to use automated compounders for admixing parenteral nutritional solutions. In such compounders, solution containers are hung on the compounder, and through the use of pumps or valves the solutions therein are compounded to create a final solution including all of the necessary components, e.g. lipids, carbohydrates and amino acids. U.S. Pat. Nos. 4,653,010, and 4,467,944 disclose embodiments of such automated compounders.

SUMMARY OF THE INVENTION

The present invention provides containers and methods for storing medical solutions. More specifically, the present invention provides containers and methods for storing components that are to be admixed together to create a final solution, one of the components comprising a lipid.

To this end, the present invention provides a container including an interior defining at least two chambers. The first chamber includes a lipid containing liquid. The second chamber includes a liquid that does not include a lipid. The first and second chambers are separated by an openable seal.

In an embodiment the openable seal is a peelable seal.

In an embodiment the second chamber includes at least one component selected from the group consisting of dextrose, amino acids, water, vitamins, and electrolytes.

In an embodiment three separate chambers are provided that are separated by two openable seals.

In an embodiment each of the first and second chambers includes an access port to allow selective fluid communication with the chamber.

In an embodiment the liquid in the second chamber includes amino acids and the third chamber includes in an interior thereof a liquid including dextrose.

In an embodiment the access ports are constructed from a material not including polyvinyl chloride.

In another embodiment of the present invention, a container is provided having a body constructed from a flexible plastic material. that does not include polyvinyl chloride. The body defines at least a first and second chamber. The first chamber includes a lipid containing liquid and the second chamber includes a liquid including at least one component selected from the group consisting of: amino acids; dextrose; vitamins; and electrolytes. An openable seal is located between the first and the second chamber.

The present invention also provides a method for providing nutrition to a patient comprising the steps of: providing a container including at least two chambers, a first chamber including a lipid containing liquid and a second chamber including a second liquid that does not include a lipid, the chambers being separated by an openable seal; opening the seal between the first and second chambers; mixing the first and second liquids within an interior of the container; and administering a resultant liquid to a patient.

In an embodiment, the resultant liquid is administered parenterally to the patient.

In another embodiment of the present invention, a method for providing hyperalimentation to a patient is provided comprising the steps of: providing a container including a lipid component, a dextrose component, and an amino acid component, each of the components being housed in a separate chamber; mixing the components in an interior of the container; and administering a resultant fluid to a patient.

Furthermore, in an embodiment of the present invention a flexible plastic container is provided that includes a liquid that contains a lipid.

Still further, the present invention provides a method for providing hyperalimentation solutions to a healthcare facility comprising the steps of: providing a multi-chambered container; filling one of the chambers with a liquid including a lipid; filling a separate of the chambers with a liquid including amino acids; filling a different of the chambers with a liquid including dextrose; and providing the multi-chambered container to a healthcare facility.

In an embodiment, the chambers are filled substantially simultaneously.

In an embodiment, the amino acids are first filled into the container.

In an embodiment, the dextrose is first filled into the container.

In an embodiment, the method includes the step of sterilizing a filled container.

In an embodiment, the filled container is autoclaved.

An advantage of the present invention is that it provides a container for storing all of the base components for a total parenteral nutrition solution.

Additionally, an advantage of the present invention is that it provides a container that includes, in an embodiment, electrolytes in amino acids, calcium in dextrose, and trace elements in dextrose.

Still further, an advantage of the present invention is to provide a container for storing medical solutions that include a lipid.

Furthermore, an advantage of the present invention is to provide a method for improving the safety of compounding medical solutions.

Further, an advantage of the present invention is to provide a container and method for preparing parenteral nutrition solutions that does not require an automated compounder.

Another advantage of the present invention is to provide a method and container for decreasing waste of unused customized total parenteral nutrition solutions.

Moreover, an advantage of the present invention is to provide a method and container for decreasing the turn around time between ordering and administering medical solutions such as nutritional solutions to patients.

Furthermore, an advantage of the present invention is to provide a safer method for providing total parenteral nutrition to patients.

Still further, an advantage of the present invention is to reduce pharmacy labor in compounding nutritional solutions.

Still, an advantage of the present invention is to help simplify the ordering of total parenteral nutrition solutions.

Moreover, an advantage of the present invention is it reduces the risk of contamination during the preparation of medical solutions by minimizing pharmacy manipulations.

Additional features and advantages of the present invention are described in, and will be apparent from, the detailed description of the presently preferred embodiments and from the drawings.

BRIEF DESCRIPTION OF THE DRAWINGS

FIG. 1 illustrates a perspective view of an embodiment of the container of the present invention.

FIG. 2 illustrates a perspective view of another embodiment of the container of the present invention.

FIG. 3 illustrates a cross sectional view of an embodiment of the film used to construct the container of the present invention.

FIG. 4 illustrates an end view of an embodiment of a die used to create the seal of the container of FIG. 1.

DETAILED DESCRIPTION OF THE PRESENTLY PREFERRED EMBODIMENTS

Figure 5:
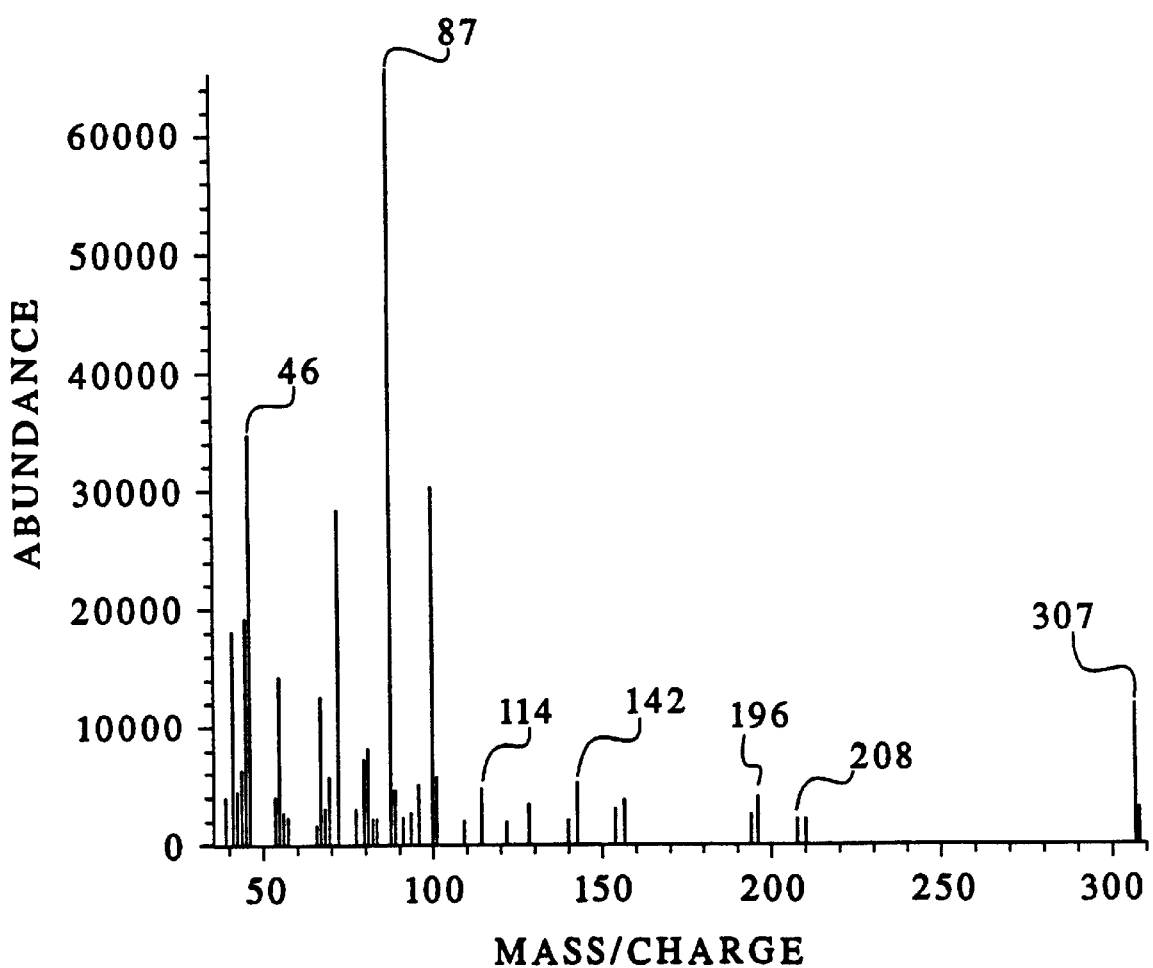
FIG. 5 illustrates total ion chromagrams generated from sample extracts pursuant to Example No. 1.

The present invention preferably provides a multiple chamber container that can be used to house multiple liquid components of a product that are to be stored separately prior to use. Due to the unique structure of the present invention, the components can be mixed prior to use and the container, as well as the method, allows the storage of lipids in the same structure with other components. Thus, in an embodiment, the present invention allows for the storage of at least three base solutions of a hyperalimentation solution in a single container prior to use. It should be noted that although in a preferred embodiment the present invention provides multi-chambered containers, pursuant to the present invention a container having a single chamber containing a lipid containing liquid is contemplated.

Referring now to FIG. 1, an embodiment of the present invention is illustrated. Preferably, the container 10 includes, at least three chambers 12, 14, and 16. The chambers 12, 14, and 16 are designed for the separate storage of liquids and/or solutions. It should be noted that although three chambers 12, 14, and 16 are present in the embodiment of the invention illustrated in FIG. 1, more or less chambers can be used.

Preferably, peelable seals 18 and 20 are provided between the chambers 12 and 14 and 14 and 16 respectively. Such a peelable seal is disclosed in U.S. patent application Ser. No. 08/033,233 filed on Mar. 16, 1993 entitled "PEELABLE SEAL AND CONTAINER HAVING SAME". The disclosure of that application is hereby incorporated herein by reference. The peelable seals allow for the selective opening of the chambers to allow for the selective mixing of the liquids contained therein.

Pursuant to the present invention, at least one of the chambers 16 can store a liquid that includes lipids. In a preferred embodiment the container 10 includes in the first chamber 12 dextrose, in the second chamber amino acids 14, and in the third chamber lipids 16.

Referring now to FIG. 2, another embodiment of the present invention is illustrated. Similar to the embodiment illustrated in FIG. 1 preferably, the container 110 includes, at least three chambers 112, 114, and 116. The chambers 112, 114, and 116 are designed for the separate storage of liquids and/or solutions. It should be noted that although three chambers 112, 114, and 116 are present in the embodiment of the invention illustrated in FIG. 2, more or less chambers can be used. As in the embodiments of FIG. 1, preferably peelable seals 118 and 120 are provided between the chambers 112 and 114 and 114 and 116 respectively.

Referring now to FIG. 3 a cross sectional view of an embodiment of the film 21 used to construct the containers 10 and 110 of the present invention is illustrated. In the preferred embodiment illustrated, the film 21 includes, a four layer 22, 24, 26, and 28 structure.

In this regard, in the illustrated embodiment, the outer, or first layer 22 is constructed from a polyester material such as PCCE copolyester. If desired, other high melting temperature flexible materials can be used. A PCCE copolyester material can be purchased from Eastman Kodak under the designation Ecdel 9965. A typical thickness of outer layer 22 may be, for example, from 0.39 mil to 0.71 mil, e.g., 0.55 mil.

A tie layer 24 is provided to secure the first layer 22 to a third layer 26. Preferably the tie layer is a highly reactive polymer adhesive such as EVA copolymer chemically modified with maleic acid. Such a material is available from DuPont under the name Bynel E-361. The tie layer 24 may have a varied thickness for example from 0.20 mils to 0.60 mils, e.g., 0.40 mils.

The third layer 26 preferably is a RF responsive polymer, such as EVA copolymer. Such a material is available from DuPont under the name Elvax 3182-2. Preferably the third layer has a thickness of about 5.56 mils to about 6.84 mils, e.g., 6.20 mils.

This film also includes a sealant layer 28 constructed of 1) a bulk polyolefin that is thermally stable at sterilization temperatures, yet melts below the outside layer melting temperature; such polymers are preferably polypropylene-ethylene copolymers, such as Z9450 from Fina Oil and Chemical; and 2) a thermoplastic elastomer which produces a more flexible and free radical resistant sealant layer and gives the sealant layer two melt points with the elastomer having the lower value; such polymers preferably are styrene-ethylene-butene-styrene block copolymers such as Kraton G-1652 from Shell Oil and Chemical. The sealant layer preferably has a thickness of from about 1.28 mils to about 1.92 mils, e.g., 1.60 mils.

The sealant layer 28 is adjacent the solution side of the container 10 such that when the seal is ruptured, communication is provided between the chambers, e.g. 12 and 14.

As constructed the four-layer film illustrated in FIG. 3 has at least one RF-responsive layer 26 and one non-RF responsive layer 28. To create the seals a RF field heats a seal bar (described hereinafter with reference to FIG. 4) which heats the RF-responsive layer 26 which, in turn, heats the non-RF responsive layer 28 to soften the layer, but not liquify same. A resulting cohesive bond develops from contact between the non-RF responsive layer 28 of the sheet 30 and a corresponding non-RF responsive layer 28 of the sheet 30a, but fusion between the layers, which can cause permanent bonding, does not occur.

To form the peelable seal using radio frequency welding or other forms of heating sealing technology in a preferred embodiment a die 40, illustrated in FIG. 4, is used. The die 40 includes the seal bar 42 which is formed to project substantially perpendicularly to a base 44 on which the seal bar 42 is integrally mounted. The base 44 can be further secured to manufacturing components (not shown) by fasteners (not shown) inserted through holes in the base 44. The seal bar 44 of the die 40 is used to form the peelable seal wherein the seal bar 42 can be energized using RF energy.

The seal bar 42, as illustrated, has a substantially equal width, designated as "x" in FIG. 4, of, in the preferred embodiment, approximately ⅜ inches. The seal bar 42 further includes radiused corners 48 and grooves 49 to control activation forces and increase consistency of the seal. During sterilization temperatures, the inside layer, in intimate contact with itself, will weld together due to fusion of the lower melting point material. This phenomenon allows the die 42 to have a lower surface area, thus giving more control of pressure parameters and reducing the risk of fusing the higher melting point material which would result in actual heat seals. In the preferred embodiment illustrated, the radial dimension is 1/16". The peelable seal formed using the seal bar 42 of the present invention results in a bond which is less likely to break due to external forces exerted thereon.

By way of example, and not limitation, an example of how the peel seal is created will be given. In a preferred embodiment, the inner layer includes SEBS and ethylene polypropylene. SEBS has a melting point of approximately 127° C. and ethylene polypropylene approximately 140° C. The die, illustrated in FIG. 4, is initially heated to a temperature of 50° C. and urged against the container in a position to create the desired seal. The die is then energized with sufficient RF energy to reach a temperature of between 128° C. and 131° C. This creates the peel seal.

In a preferred embodiment, the peel seals are created so that they are permanent seals for the length of the container 10.

Pursuant to the present invention, and in view of the structure of the container 10, the container can house lipids. In this regard, the lipids will not leach any components from the film used to construct the container 10. The present invention also allows the lipids to be filled into the container 10 and the container retorted (sterilized) Heretofore, commercially available lipids could not be stored in plastic containers and were always retorted in glass.

As illustrated in FIG. 1, preferably, each chamber 12, 14, and 16 can include an access or tubular port 31, 32, and 34. In the illustrated embodiment, port 31 is an injection site and port 32 is an administration port. The ports 31 and 32 can be constructed from any number of methods. For example, in an embodiment the ports 31 and 32, for chambers 12 and 14, are constructed from a clear PVC membrane plasticized with DEHP. To maintain sterility of the interior of the ports 31 and 32, an injection cap can be secured over the port.

However, with respect to chamber 18, that is designed to house a lipid, the access port 34 is constructed from a non-PVC containing material. For example, a blend, preferably of polypropylene, SEBS, and EVA can be used. In a preferred embodiment the port 34 is a three layer co-extrusion with the following formulation:

External layer (125μ):
35% PP Fortilene 4265
25% Tafmer A4085
10% Kraton FG1924
10% Macromelt TPX16-159
20% EVA Escorene UL00328 (28% VA)

Medium layer (580μ)
35% PP Fortilene 4265
25% Tafmer A4085
10% Kraton FG1924
10% Macromelt TPX16-159
20% EVA Escorene UL00328 (28% VA)

Internal layer (125μ)
50% EVA Escorene UL00119 (19% VA)
50% EVA Escorene UL00328 (28% VA)

In a preferred embodiment, all of the access ports 31, 32, and 34 are constructed from a non-PVC material such as that set forth above.

The tubular ports 31, 32, and 34 are mounted in the container to allow fluid communication with the container 10 and specifically the chambers 12, 14, and 16. To this end the ports 31, 32, and 34 can include a membrane that is pierced by, for example, a cannula or a spike of an administration set for delivery of the contents of the container through the administration set to the patient. Of course, more or less than three ports can be used.

In an embodiment, an additive port (not shown) is located at an end of the container 10 opposite the access ports 31, 32, and 34. The additive port allows the addition to the container of micro ingredients or micro nutrients.

Preferably, all the ports are located on one end of the container. This may allow for more efficient manufacturing and allows filling of all chambers at one time.

In an embodiment the container 10 is a 3 liter unit with three chambers separated by two peel seals. The chambers of the container, in an embodiment, are designed to contain dextrose (10–70%), amino acids (5.5–20%, with or without electrolytes) and a lipid (10%–30%). The filled container is designed to be placed in an oxygen barrier overpouch and autoclaved. Prior to use, the user will open the seals and mix the solutions. It is believed that such a container 10 will have a shelf life of at least twelve months.

It should also be noted that the container 10 may be prepackaged with trace elements, vitamins, and/or electrolytes. For example trace elements could be packaged in the same chamber with dextrose.

By way of example and not limitation examples of containers for providing total parenteral nutrition to patients will now be given.

| Chamber sizes (mL) | Corresponding formulas |
|---|---|
| 800/225/800 | Acute 1, Acute 1E, Acute 2E, Acute 3, Acute 3E and Non-acute 1E |
| 800/400/800 | Acute 4E (High lipid) and Peripheral formula 1 |

| | chamber conc. | final conc. | vol | grams | g/kg[1] | kcal | NPC | NPC/kg | kcal | kcal/kg | % NPC as lipid |
|---|---|---|---|---|---|---|---|---|---|---|---|
| Acute 1 = the formula below without electrolytes | | | | | | | | | | | 800/225/800 config. |
| Acute 1E = the formula below with electrolytes | | | | | | | | | | | |
| AA | 15.0% | 6.6% | 800 | 120 | 1.7 | 480 | | | | | |
| lipid | 20.0% | 2.5% | 225 | 45 | | 405 | | | | | |
| dextrose | 50.0% | 21.9% | 800 | 400 | | 1,360 | 1,765 | 25 | 2,245 | 32 | 23% |
| | | | 1825 | | | | | | | | |
| Acute 2E (with electrolyte) | | | | | | | | | | | 800/225/800 config. |
| AA | 13.0% | 5.7% | 800 | 104 | 1.5 | 416 | | | | | |
| lipid | 20.0% | 2.5% | 225 | 45 | | 405 | | | | | |
| dextrose | 50.0% | 21.9% | 800 | 400 | | 1,360 | 1,765 | 25 | 2,181 | 31 | 23% |
| | | | 1825 | | | | | | | | |
| Acute 3 = the formula below without electrolytes | | | | | | | | | | | 800/225/800 config. |
| Acute 3E = the formula below with electrolytes | | | | | | | | | | | |
| AA | 10.0% | 4.4% | 800 | 80 | 1.1 | 320 | | | | | |
| lipid | 20.0% | 2.5% | 225 | 45 | | 405 | | | | | |
| dextrose | 50.0% | 21.9% | 800 | 400 | | 1,360 | 1,765 | 25 | 2,085 | 30 | 23% |
| | | | 1825 | | | | | | | | |
| Acute 4E (with electrolytes) | | | | | | | | | | | 800/400/800 config. |
| High lipid formula | | | | | | | | | | | |
| AA | 13.0% | 5.2% | 800 | 104 | 1.5 | 416 | | | | | |

-continued

| | | | | | | | | | | |
|---|---|---|---|---|---|---|---|---|---|---|
| lipid | 20.0% | 4.0% | 400 | 80 | | 720 | | | | |
| dextrose | 30.0% | 12.0% | 800 | 240 | | 816 | 1,536 | 22 | 1,952 | 28 | 47% |
| | | | 2000 | | | | | | | |
| Non-acute 1E (with electrolytes) | | | | | | | | | 800/225/800 config. | |
| AA | 8.5% | 3.7% | 800 | 68 | 1.0 | 272 | | | | |
| lipid | 20.0% | 2.5% | 225 | 45 | | 405 | | | | |
| dextrose | 50.0% | 21.9% | 800 | 400 | | 1,360 | 1,765 | 25 | 2,037 | 29 | 23% |
| | | | 1825 | | | | | | | |
| Peripheral 1E (with electrolytes) | | | | | | | | | 800/400/800 config. | |
| AA | 8.5% | 3.4% | 800 | 68 | 1.0 | 272 | | | | |
| lipid | 10.0% | 2.0% | 400 | 40 | | 360 | | | | |
| dextrose | 10.0% | 4.0% | 800 | 80 | | 272 | 632 | 9 | 904 | 13 | 57% |

Osmolarity: approx. 670 mOsm/L

[1]Assumes a 70 kg patient.

It is believed that these eight containers could meet 80–90% of all adult patients.

By way of example and not limitation examples of the present invention will now be given:

EXAMPLE NO. 1

The purpose of this study was to provide preliminary extractive information regarding an embodiment of the container of the present invention for the long-term storage of retorted lipid emulsions.

In this study, the test articles were 500-ml units prepared from the film set forth previously in the specification with two non-PVC port tubes. The units were filled with 20% lipid emulsion, placed in a foil overpouch, purged with nitrogen and steam sterilized for either 30, 40 or 50 minutes. Aliquots of the 20% lipid emulsion stored in the test articles, 20% lipid emulsion stored in glass bottles, and 20% lipid emulsion stored in glass bottles spiked with target extractives were analyzed for target extractives.

Irganox® 1076, 2-ethylhexanoic acid, and 25-Crown-5 in the lipid emulsion samples were at levels below the estimated detection limits of the method, 0.57 µg/mL, 0.44 µg/mL and 0.24 µg/mL, respectively. 1,2-Bis(sec-butoxycarboxy)ethane (SBCE) and 2,6-di-t-butyle-4-methylphenol (BHT) were detected in the samples at levels near the estimated detection limits of 0.28 µg/mL and 0.095 µg/mL, respectively. There were no apparent differences in the extractive levels due to the length of sterilization. Additionally, no non-targeted extractives were seen in a total ion chromatogram of an extract of 20% lipid emulsion stored in a test article.

To enhance the sensitivity for the target extractives, the lipid emulsion extracts were analyzed using selective ion monitoring mass spectral detection, while the total ion monitoring mass spectrometry was used to screen the extracts for additional non-targeted compounds. In both analyses, the factor limiting the sensitivity of this method is concentrating the 20% lipid emulsion. In principle, the sensitivity of this methodology will be greater in the three-chamber container system due to the lower lipid emulsion concentration in the final solution.

In other studies, the levels of target extractives were determined. The extractive levels in the lipid emulsion solutions were determined by extracting the lipid emulsion and analyzing by gas chromatography with selected ion mass spectrometry. The intent of this study was to provide preliminary information on the accumulation of 2-ethylhexanoic acid, 1,2-bis(sec-butoxycarboxy)ethane (SBCE), 2,6-di-t-butyle-4-methylphenol (BHT), 25-crown-5 ether and Irganox® 1076 in 20% lipid emulsion retorted in containers. Additionally, a sample extract was analyzed by gas chromatography with total ion mass spectrometry.

These units had two non-PVC port tubes which were sealed with aluminum crimps. The film is co-extruded, with the following configuration: polypropylene-Kraton® (solution contact)/poly(ethylene vinyl acetate) (EVA)/maleic anhydride modified EVA (tie layer)/PCCE. The PCCE is poly(cyclohexylenedimethylene cyclohexanedicarboxylate) copolymer with tetramethylene glycol. The test articles were filled with 20% lipid emulsion, placed in a foil overpouch, purged with nitrogen and sealed. The units were then steam sterilized for either 30, 40 or 50 minutes and analyzed.

The following sample extraction methodology was developed as part of the study. 1.0-mL aliquot of the 20% lipid emulsion sample and of the 20% lipid emulsion stored in glass were transferred into 125-mL separatory funnels containing 15 mL of 0.9% sodium chloride. A 1.0-mL, volumetrically pipetted, aliquot of a 31.3 µg/mL di-n-octyl phthalate (DOP) internal standard solution, 20 mL of methanol and 40 mL of methylene chloride were added. The samples were extracted and the methylene chloride was collected in a 200-mL Zymark TurboVap® collection tube. The samples were then extracted with a second 40-mL portion of methylene chloride. The methylene chloride fractions were pooled, concentrated to approximately 1 mL under a stream of $N_2$ and analyzed.

The GC standard was prepared as follows: into 125-mL separatory funnels containing 1 mL of the 20% lipid emulsion which was stored in glass and 15 mL of 0.9% sodium chloride, 1.0-mL aliquots of each standard solution were added. The standards were extracted and analyzed. Additionally, the extract of the STD-H spiked lipid emulsion was analyzed.

| | Concentration of Standards, (µg/mL) | | | | |
|---|---|---|---|---|---|
| Standard | 2-EHA | SBCE | BHT | Irganox ®1076 | 25-Crown-5 |
| STD-H | 268 | 66.8 | 83.2 | 99.6 | 79.2 |
| STD-MH | 66.9 | 16.7 | 20.8 | 24.9 | 19.8 |

-continued

Concentration of Standards, (µg/mL)

| Standard | 2-EHA | SBCE | BHT | Irganox ®1076 | 25-Crown-5 |
|---|---|---|---|---|---|
| STD-ML | 40.1 | 10.0 | 12.5 | 14.9 | 11.9 |
| STD-L | 8.03 | 2.00 | 2.50 | 2.99 | 2.38 |

Gas chromatography with selected ion monitoring mass spectral detection (GC/MS-SIM) was used. The instrument conditions were as follows:

| | |
|---|---|
| Gas Chromatograph: | HP5890 |
| Detector: | Mass Selective Detector HP5790 |
| Column: | DB-5, 30 m × 0.32 mm × 0.25 µm (film) |
| Program: | 40° for 1 min, 5° C./min to 210° C., 20° C./min to 300° C. held for 25 min. |
| Injection port: | 250° C., with a glass wool plug. |
| Transfer Line: | 310° C. |
| Injection volume: | 2 µL, splitless for 30 sec. |
| Mode: | EI+ |
| Ions monitored (m/z): | |
| Time on (min): | |
| 5.00 (2-EHA) | 73, 88 and 116 |
| 20.00 (BHT) | 57, 205 and 220 |
| 27.00 (SBCE) | 45, 89 and 151 |
| 30.00 (25-Crown-5) | 71, 72 and 100 |
| 42.30 (DEHP) | 149, 167 and 279 |
| 46.00 (Irganox ®1076) | 219, 515 and 530 |
| Dwell Time: | 100 msec. |

Gas chromatography with total ion mass spectral detection (GC/MS):

| | |
|---|---|
| Gas Chromatograph: | HP5890 |
| Detector: | Mass Selective Detector HP5790 |
| Column: | DB-5, 30 m × 0.32 mm × 0.25 µm (film) |
| Program: | 40° for 1 min, 5° C./min to 210° C., 20° C./min to 300° C. held for 25 min. |
| Injection port: | 250° C., with a glass wool plug. |
| Transfer Line: | 310° C. |
| Injection volume: | 2 µL, splitless for 30 sec. |
| Mode: | EI+ |
| Scan Range (m/z): | 35-650 |

The levels of 2-EHA, Irganox® 1076 and 25-Crown-5 in the lipid emulsion samples were below the estimated detection limits of the methodology. The detection limits were calculated at three times the signal to noise ratio of the spiked standard (STD-L).

At the GC retention time of BHT, small peaks were observed in the extracts of the sample and control lipid emulsion. At the GC retention time of SBCE, small peaks were observed in the extracts of the samples. The concentrations of BHT and SBCE in the lipid emulsion were then determined from the relative response of the analyte to the internal standard in the spiked lipid standard (STD-L).

These BHT and SBCE levels were near the estimated detection limits of the method. The spike recovery for the individual target extractives were not calculated. The level of each target extractive in the 20% lipid emulsion samples is listed in Table 1. The estimated detection limit for each extractive in 20% lipid emulsion is listed in Table 2.

TABLE 1

Levels of Target Extractives in 20% Lipid Emulsion Samples and Control, µg/mL.

| Sample | 2-EHA | SBCE | BHT | Irganox ® 1076 | 25-Crown-5 |
|---|---|---|---|---|---|
| 149014.30 | <d.1. | 0.30 | 0.14 | <d.1. | <d.1. |
| 149014.40 | <d.1. | 0.23 | 0.09 | <d.1. | <d.1. |
| 149014.50 | <d.1. | 0.22 | 0.08 | <d.1. | <d.1. |
| Control | <d.1. | <d.1. | 0.03 | <d.1. | <d.1. |

Where: <d.1. is less than the detection limit listed in Table 2.

TABLE 2

Estimated Detection Limit for Target Extractives in 20% Lipid Emulsion, µg/mL.

| Analyte | Detection Limit |
|---|---|
| 2-EHA | 0.44 µg/mL |
| SBCE | 0.28 µg/mL |
| BHT | 0.095 µg/mL |
| Irganox ®1076 | 0.57 µg/mL |
| 25-Crown-5 | 0.24 µg/mL |

No additional extractives were observed in the total ion monitoring GC/MS analysis of the extracted lipid emulsion sample.

The study provided preliminary data on the accumulation of target extractives in retorted 20% lipid emulsion. 2-EHA, Irganox® 1076 and 25-Crown-5 in the lipid emulsion samples were at levels below the detection limit of the methodology. SBCE and BHT were detected in the samples at levels near the detection limits. There were no apparent differences in the extractive levels due to the length of sterilization. Additionally, no non-targeted extractives were seen in the total ion chromatograms of the extracts of the 20% lipid emulsion.

To enhance the sensitivity for the target extractives, the lipid emulsion extracts were analyzed using selective ion monitoring mass spectral detection, while the total ion monitoring mass spectrometry was used to screen the extracts for additional non-targeted compounds. In both analyses, the factor limiting the sensitivity of the method is the inability to concentrate the oil extracted from the 20% lipid emulsion. In principle, the sensitivity of this methodology will be greater in the three-chambered RTU container system due to the lower lipid emulsion concentration in the mixed solution.

EXAMPLE NO. 2

This example analyzed an embodiment of the container system of the present invention for the long-term storage and intravenous administration of dextrose, amino acids and lipid emulsion. An embodiment of the container is a 2-L non-poly(vinylchloride) (PVC) unit with three chambers separated by two peelable seals. One chamber will contain 800 mL of a dextrose solution (10–70%), the second chamber will contain 800 mL of an amino acid solution (5.5–10%), with or without electrolytes) and the third chamber will contain up to 400 mL of lipid emulsion (10 or 30%). The filled container will be placed in a foil overpouch, purged with nitrogen and steam sterilized. Prior to use, the customer will break the peel seals and mix the three solutions. The maximal lipid emulsion concentration in the resulting total parenteral nutrition (TPN) solution is 4%.

The container is constructed from a co-extruded film with the following configuration: polypropylene-Kraton® (solution contact)/poly(ethylene vinyl acetate) (EVA)/ maleic anhydride modified EVA (tie layer)/PCCE. The PCCE is poly(cyclohexylene-dimethylenecyclohexanedicarboxylate) copolymer with tetramethylene glycol. The container is fitted with PVC containing port and membrane tube assemblies on the chambers containing the dextrose and amino acid solutions and a non-PVC port and plug assembly on the chamber containing the lipid emulsion solution.

The test articles were filled as follows: 1) the chamber of the container to be used for the dextrose solution was filled with 800 mL of water for injection, 2) the chamber of the container to be used for the amino acid solution was filled with 800 mL of water for injection, and 3) the chamber of the container to be used for the lipid emulsion was filled with 400 mL of 20% lipid emulsion. The filled units were placed in foil overpouches and autoclaved. A total of twelve units were produced for the study.

The study design follows previously developed methodologies for: 2,6-di-t-butyl-4-methylphenol (BHT), 2,6-di-t-butyl-4-ethylphenol 1,2-bis(sec-butoxycarboxy)ethane, 25-crown-5 ether, isopropyl myristate, 2-ethylhexanoic acid, Irganox® 1010, Irganox® 1076, A0330, 1,2-bis(2-ethylhexyl)phthalate (DEHP), aluminum, volatile organic compounds and propylene and ethylene vinyl acetate oligomers in lipid containing solutions. To access the extractable burden of the container, the peel seals of the three chambered test articles were opened and the three solutions were mixed prior to all analyses except for cyclohexanone. Due to an expected loss of cyclohexanone during the lipid extraction procedure, only the peel seal separating the water-filled chambers was opened, mixed and assayed for cyclohexanone.

The volatile organic compounds, semi-volatile compounds, aluminum, antioxidants, and oligomeric propylene and ethylene vinyl acetate assays were performed on unit numbers 601, 602, and 604. Immediately after sampling the test articles for volatile organic compounds, the units were allowed to stand at ambient temperature for an additional 48 hours to mimic the potential interaction of the lipid solution with the entire container system expected from product handling and administration. The solutions from the three test articles were then sampled for aluminum, transferred into separate glass containers, and stored under refrigeration until required for analyses. The cyclohexanone assay was performed on a sample of the pooled water from the amino acid and dextrose chambers of unit numbers.

Lipid emulsion control solutions diluted with NANOpure water to a nominal concentration of 4%, along with diluted lipid emulsion solutions spiked with known targeted compounds were analyzed as appropriate.

Two aliquots from the three containers and the control lipid emulsion were analyzed for volatile organic compounds by purge and trap gas chromatography with mass spectrometric detection (GC/MS) using the method listed in Table 3 below.

The major volatile organic compound observed in the total ion chromatograms was cyclohexanone. The levels of cyclohexanone in the water-filled chambers were determined in three containers. In addition to the cyclohexanone, 4-methyl-2-pentanone and toluene were detected as compounds unique to the lipid emulsion stored in the container system. The r-methyl-2-pentanone and toluene detected in the sample solutions had the same GC retention time and mass spectra as that of the authentic standard materials.

In an earlier study, 4-methyl-2-pentanone and toluene were identified as materials which may accumulate in solution from the hot stamp foil used to print the container. The levels of the 4-methyl-2-pentanone and toluene in the lipid solution stored in the container were determined from the response of the $d_5$-chlorobenzene internal standard. The levels of 4-methyl-2-pentanone and toluene in the lipid solution stored containers are as follows:

| Unit Sample | 4-methyl-2-pentanone, µg/mL | toluene, µg/mL |
|---|---|---|
| 601-1 | 0.028 | 0.033 |
| 601-2 | 0.029 | 0.032 |
| 602-1 | 0.034 | 0.036 |
| 602-2 | 0.034 | 0.035 |
| 604-1 | 0.032 | 0.034 |
| 604-2 | 0.034 | 0.036 |

The levels of the targeted semivolatile compounds 2,6-di-t-butyl-4-methyl-phenol (BHT), 2,6-di-t-butyl-4-ethylphenol (DtBEP) 1,2-bis(sec-butoxycarboxy)ethane (SBCE), 25-crown-5 ether (25-C-5), isopropyl myristate (IPM), 2-ethylhexanoic acid (2-EHA), and 1,2-bis(2-ethylehexyl)phthalate (DEHP) were determined in two aliquots from each of three units, the control lipid and emulsion spiked with the known targets extractives.

A 5.0-mL aliquot of the lipid emulsion sample and of the 4% lipid emulsion control were transferred into 125-mL separatory funnels containing 15 mL of 0.9% sodium chloride. A 1.0-mL, volumetrically pipetted, aliquot of a 30.3 mg/mL di-n-octyl phthalate (DOP) internal standard solution, 20 mL of methanol and 40 mL of methylene chloride were added. The samples were extracted and the methylene chloride was collected in a 200-mL Zymar Turbo Vap® collection tube. The samples were then extracted with a second 40-mL portion of methylene chloride. The methylene chloride fractions were pooled, concentrated to approximately 1 mL under a stream of $N_2$ and analyzed by the GC/MS-SIM system listed in Table 4.

Spiked lipid controls were prepared by adding the target extractive compounds into the 4% control lipid emulsion resulting in the following concentrations (µg/mL):

| Spike | 2-EHA | BHT | DtBEP | IPM | SBCE | 25-C-5 | DEHP | Irganox ® 1076 |
|---|---|---|---|---|---|---|---|---|
| Spike-L | 0.58 | 0.16 | 0.17 | 0.17 | 0.17 | 0.18 | 0.20 | 0.20 |
| Spike-M | 2.9 | 0.82 | 0.84 | 0.85 | 0.84 | 0.88 | 1.0 | 0.98 |
| Spike-H | 5.8 | 1.6 | 1.7 | 1.7 | 1.7 | 1.8 | 2.0 | 2.0 |

The spiked lipid controls were then extracted, concentrated and analyzed in the same manner as that used for the samples.

To screen for potential non-targeted extractives, an extract from each of the three units and the control lipid was analyzed in a total ion scanning GC/MS mode using the instrument conditions listed in Table 5.

Responses for the target extractives were detected at each spike level with the exception of the 0.58 µg/mL 2-EHA spike and the Irganox® 1076. The lower sensitivity for 2-EHA results in a corresponding higher detection limit for 2-EHA. No Irganox® 1076 was observed in the GC/MS analysis of the spiked lipid control solutions of the standard solutions which were used to spike the control lipid emulsion. This result indicates that the GC/MS conditions which were utilized may have not been suitable for detecting Irganox® 1076. In an earlier study, Irganox® 1076 was not detected in samples of 20% lipid emulsion stored and retorted in containers prepared from the film at a detection limit of 0.57 µg/mL.

With the exception of DEHP, the concentration of the target extractives in the extracts from the container were either not detected or observed at a level significantly less than that of the lowest level spiked. The DEHP levels in the sample extracts were near the lowest level spiked with the exception of a single replicate at 2.1 µg/mL.

For each target extractive, detection limits were calculated at three times the signal to noise ratio in the chromatogram of the lowest spike concentration for which a response was observed. In samples where the response for a target extractives was observed above this detection limit, the concentration of the extractive was determined from the linear regression analysis of the response of the spiked lipid extracts at the three levels analyzed.

Since the detection limit and quantitation calculations were conducted using the responses from the spiked lipid controls, no corrections for spike recovery were required or performed. The level of the target extractives observed in duplicate aliquots from the three containers and calculated detection limits, in µg/mL, are as follows:

| Unit-sample | 2-EHA | BHT | DtBEP | IPM | SBCE | 25-C-5 | DEHP | Irganox® 1076 |
|---|---|---|---|---|---|---|---|---|
| 601-1 | <d1(a) | 0.029 | <d1 | <d1 | 0.084 | <d1 | 0.11 | N/A(b) |
| 601-2 | <d1 | 0.045 | <d1 | <d1 | 0.097 | <d1 | 0.11 | N/A |
| 602-1 | <d1 | 0.047 | <d1 | <d1 | 0.10 | <d1 | 2.1 | N/A |
| 602-2 | <d1 | 0.049 | <d1 | <d1 | 0.11 | <d1 | 0.086 | N/A |
| 604-1 | <d1 | 0.050 | <d1 | <d1 | 0.11 | <d1 | 0.10 | N/A |
| 604-2 | <d1 | 0.049 | <d1 | <d1 | 0.11 | <d1 | 0.27 | N/A |
| Detection Limit | 0.17 | 0.012 | 0.011 | 0.018 | 0.015 | 0.010 | 0.010 | N/A |

(a) Where, d1 indicates a level less than the detection limit
(b) Where N/A indicates that no values could be determined.

Figure 6:
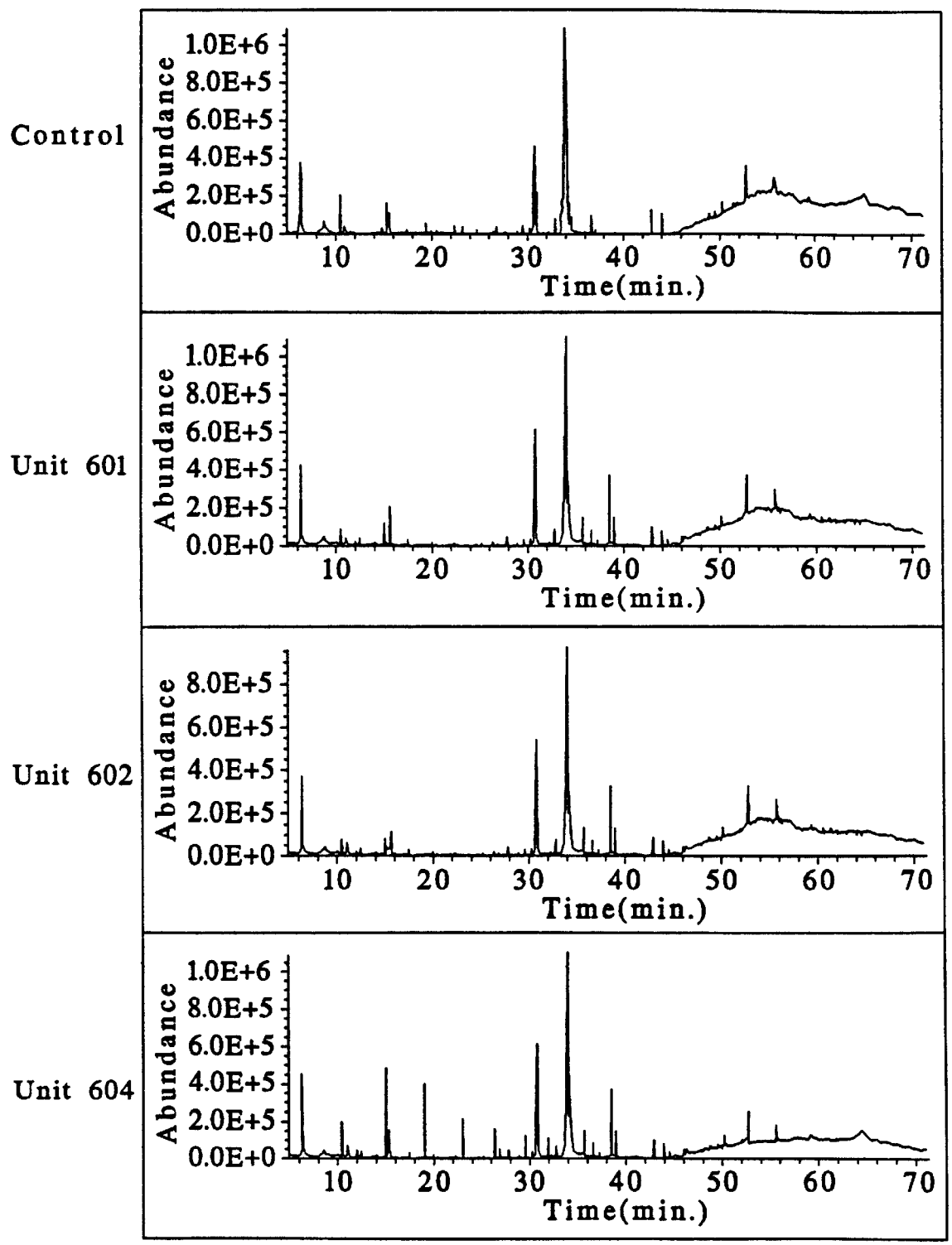
FIG. 6 illustrates a mass spectrum of peak B of FIG. 5.

To screen for potential non-targeted extractives, the total ion chromatograms generated for the sample extracts were compared to that of the control (See FIG. 5). Four peaks (labeled A, B, C and D in FIG. 5) unique to the samples were observed in the sample chromatograms. Since these peaks were only observed in the lipid solutions stored in the containers, these compounds appear to be non-targeted. extractives related to the c container system. The mass spectrum of peak B, the largest peak observed in the sample is in FIG. 6.

Cyclohexanone

The levels of cyclohexanone in duplicate aliquots of the pooled water-filled chambers from three RTU containers were determined using the direct aqueous injection gas chromatography with flame ionization detection (GC/FID). To quantitate the level of cyclohexanone in the samples, cyclohexanone standards in water were prepared at concentrations of 0.034 µg/mL, 0.135 µg/mL, 3.37 µg/mL and 6.74 µg/mL. A 10-µg/mL aliquot of a 356 µg/mL cyclopentanone standard solution was added to 1-mL aliquots of each standard and sample for use as an internal standard. The GC/FID instrument conditions are listed in Table 6.

The levels of cyclohexanone in the water-filled chambers of the three containers were determined from the linear regression line constructed from the responses of the cyclohexanone standards. The results of the cyclohexanone analysis are as follows:

| Unit Number | Cyclohexanone, µg/mL |
|---|---|
| 591 | 2.05 |
| 605 | 2.81 |
| 613 | 3.16 |

Aluminum

Samples of the lipid emulsion mixtures which were stored in the container for 48 hours at room temperature and transferred to Teflon® bottles, the 4% lipid emulsion control solution and the water control were analyzed for aluminum by graphite furnace atomic absorption spectroscopy.

No aluminum was detected in the water control at a level greater than the detection limit of 0.0009 µg/mL. The aluminum levels observed in the lipid emulsion solution stored in unit number 601 was slightly higher than that in the 4% lipid emulsion control article, while the aluminum levels in the lipid emulsion solutions stored in the unit numbers 602 and 604 were approximately the same as that observed for the 4% lipid emulsion control article. The aluminum concentrations in the sample and control articles are as follows:

| Sample/Unit Number | Aluminum, µg/mL |
|---|---|
| Water Control | <0.0009 |
| 4% Lipid control | 0.012 |
| 601 | 0.023 |
| 602 | 0.017 |
| 604 | 0.015 |

Antioxidants and Oligomeric Propylene and Ethylene Vinyl Acetate

A 50-mL aliquot of three lipid emulsion samples, in duplicate, and of the 4% lipid emulsion control were transferred into separatory funnels containing 25 mL of 0.9% sodium chloride and 60 mL of methanol. The mixture was extracted with two 90-mL portions of methylene chloride. The organic fractions were collected in 200-mL Zymark TurboVap® evaporation tubes and concentrated to remove the organic solvent. The resulting oil was transferred into 10-mL volumetric flasks and combined with tetrahydrofuran (THF) rinsings of the TurboVap® tube. The 10-mL volumetric flasks were then diluted to volume with THF.

A 3-mL aliquot of the extract was applied to a Chromatotron® thin layer chromatography system which uses a rapidly rotating silica gel plate (4 mm) to effect the separation. The samples and eluting solvent are applied to the center of the rotating plate that is at a displacement of about 45° from horizontal. As the plate spins, the solvent front advances outward and the components are separated in concentric circular bands. When the band reaches the outer edge of the plate, the eluate leaves the plate and drains through a small spout at the bottom edge of the Chromatotron® housing.

The eluate is collected by the analyst for analysis. The first three 45 mL of eluent were collected. These fractions contained the desired antioxidant and oligomeric materials. The eluent was concentrated to 1 mL under a stream of nitrogen prior to analyses.

Spiked lipid controls were prepared by adding extractive materials into the 50-mL aliquots of a 4% control lipid emulsion solution. The target extractive compounds for the antioxidant assay consisted of Irganox® 1010, Irganox® 1076 and A0330 standard materials. The antioxidants were analyzed at approximate concentrations of 0.5 µg/mL, 0.9 µg/mL and 1.8 µg/mL in the lipid emulsion. The target extractive material for the oligomeric propylene and ethylene vinyl acetate assay, consisted of an organic solvent extract of the film.

The film extracts were prepared by weighing approximately 10 grams film, cut into small pieces, into two separate Erlenmeyer flasks. A 75-mL aliquot of pentane was added to each flask and placed into a sonicator for 15 minutes. The pentane extracts were then decanted into separate round-bottom flasks. The same film was extracted two additional times with pentane. Each additional pentane extract was combined with the previous extracts in the respective flask. The pentane extracts were then evaporated to dryness under a stream of nitrogen. The residue, 73.4 mg, was dissolved in 50 mL of THF to prepare a stock standard. Dilutions of this stock standard resulted in the analysis of pentane extractable material at concentrations of 7.34 µg/mL, 14.7 µg/mL and 29.4 µg/mL in the lipid emulsion. These spiked lipid solutions were then extracted, purified on the Chromatotron® and analyzed as described for the test and control articles.

The purified extracts from the lipid emulsion mixture from the containers, control article and spiked controls were assayed for Irganox® 1010, Irganox® 1076 and A0330 antioxidants by high temperature GC and for oligomeric propylene and ethylene vinyl acetate by gel permeation chromatography (GPC) with ultraviolet (UV) and refractive index (RI) detection. The high temperature GC and gel permeation chromatography conditions are described in Tables 7 and 8, respectively.

The levels of the Irganox® 1010, Irganox® 1076 and A0330 antioxidants in the product could not be determined in aliquots from the containers units due to the presence of residual lipid emulsion in the extracts interfering with the detection. In the extracts of the samples, no oligomeric propylene or ethylene vinyl acetate was observed. A detection limit for the oligomeric propylene or ethylene vinyl acetate was calculated at three times the signal to noise ration in the GPC/RI chromatogram. The detection limit determined for the oligomeric propylene and ethylene vinyl acetate is 5.6 µg/mL.

Conclusion

Three units of the lipid emulsion mixture from a 2-L container were analyzed for volatile organic compounds, targeted and non-targeted semivolatile organic compounds, aluminum, antioxidants and oligomeric propylene and ethylene vinyl acetate. The targeted semi-volatile organic extractives included 2,6-di-t-butyl-4-methyl-phenol (BHT), 2,6-di-t-butyl-4-ethylphenol (DtBEP) 1,2-bis(sec-butoxycarboxy)ethane (SBCE), 25-crown-5 ether (25-C-5), isopropyl myristate (IPM), 2-ethylhexanoic acid (2-EHA), and 1,2-bis(2-ethylhexyl)phthalate (DEHP). The selected ion monitoring GC/MS analysis of the extracts provide enhanced sensitivity for the targeted extractives, with detection limits of typically less than 0.02 µg/mL. The amounts of volatile and targeted semivolatile compounds observed in the lipid emulsion stored in the proposed container system were present at low levels.

Of the extractives which were quantitated, chclohexanone was present in the container at the highest concentrations. Cyclohexanone is not a container system extractive, but rather a processing residual from the sealing of the port and membrane tube assemblies. These cyclohexanone levels were determined in the water-filled chambers of the three containers. The following table summarizes the concentration ranges and detection limits for the extractives in the container system.

| Compound | Concentration Range, µg/mL | Detection limit, µg/mL |
| --- | --- | --- |
| 4-methyl-2-pentanone | 0.028–0.034 | n.d (a) |
| toluene | 0.032–0.036 | n.d |
| 2,6-di-t-butyl-4-methyl-phenol | 0.029–0.050 | 0.012 |
| 2,6-di-t-butyl-4-ethylphenol | <d.1. (b) | 0.011 |
| 1,2-bis(sec-butoxycarboxy) ethane | 0.08–0.11 | 0.015 |
| 25-crown-5 ether | <d.1. | 0.010 |
| isopropyl myristate | <d.1. | 0.018 |
| 2-ethylhexanoic acid | <d.1. | 0.17 |
| 1,2-bis(2-ethylhexyl) phthalate | 0.1–2.1 | 0.010 |
| cyclohexanone | 2.05–3.16 | n.d. |
| aluminum | 0.015–0.023 | 0.0009 |
| Antioxidants (Irganox ®1010, Irganox ®1076 and AO330) | n/a (c) | n/a |
| Oligomeric propylene and ethylene vinyl acetate | <d.1. | <5.6 |

(a) n.d. indicates not determined.
(b) <d.1. indicates less than the detection limit.
(c) n/a indicates not available due to an analytical interference of the compounds of interest with residual lipid emulsion.

To screen for potential non-targeted extractive materials in the container system, the extracts from the semi-volatile analysis were analyzed by GC/MS in a total ion scanning mode. In the total ion chromatograms from the container extracts four unknown peaks were observed. Based on the mass spectral fragmentation patterns, the four compounds appear to be structurally similar. The apparent odd molecular weights, along with the presence of several even mass to charge fragment ions, suggests that the unknowns contain an odd number of nitrogen atoms.

TABLE 3

Instrumental Conditions for the Purge and Trap GC/MS Analysis

| | |
|---|---|
| Purge and Trap: | |
| Instrument: | Tekmar LSC 200 Purge and Trap. |
| Trap: | Carbopack B and Carbosieve (S III) |
| Sparge Vessel: | 5 mL, Fritless |
| Standby temperature: | 32° C. |
| Purge Time: | 8 Min. |
| Desorb Preheat Temp.: | 65° C. |
| Desorb Program: | 4.00 min. at 220° C. |
| Bake Program: | 8.00 min. at 260° C. |
| Valve Temp.: | 200° C. |
| Mount Temp.: | 75° C. |
| Transfer line Temp.: | 220° C. |
| Instrument: | Tekmar ALS 2050 Autosampler |
| Prepurge time: | 30 sec. |
| Sample pressurize time: | 30 sec. |
| Sample Transfer time: | 30 sec. |
| Internal Standard Transfer: | 75 sec. |
| Sample Loop: | 5 mL |
| Internal Standard Loop: | 10 μL |
| GC/MS: | |
| Instrument: | HP5890 Gas Chromatograph with VG Trio-1 Mass Spectrometer |
| Column: | Quadrex 007-624 Cyano-Propyl Methyl Phenyl siloxane fused silica capillary, 50 m × 0.53 mm ID × 3.0 mm (film) |
| Program: | 30° C. for 6.00 min., 10° C./min. to 180° C., held for 3.00 min. |
| Carrier: | He at approximately 3 mL/min with an open split interface. |
| Mass Range: | m/z 25–400 |

TABLE 4

Instrument Conditions for Gas Chromatography with Selected Ion Monitoring Mass Spectral Detection (GC/MS-SIM)

| | |
|---|---|
| Gas Chromatograph: | HP5890 |
| Detector: | Mass Selective Detector HP5790 |
| Column: | DB-5, 30 m × 0.25 mm × 0.1 μm (film) |
| Program: | 40° C. for 1 min, 5° C./min to 250° C., 20° C./min to 310° C. held for 25 min. |
| Injection port: | 300° C., with a glass wool plug. |
| Transfer Line: | 315° C. |
| Injection volume: | 2 μL, splitless for 30 sec. |
| Mode: | EI+ |
| Ions monitored (m/z): | |
| Time on (min): | |
| 5.00 (2-EHA) | 73, 88 and 116 |
| 16.00 (BHT) | 57, 205 and 220 |
| 20.50 (DtBEP) | 57, 219 and 234 |
| 21.60 (SBCE) | 45, 89 and 151 |
| 25.00 (IPM) | 60, 102 and 228 |
| 31.00 (25-Crown-5/DEHP) | 71 and 100/149 and 279 |

TABLE 4-continued

Instrument Conditions for Gas Chromatography with Selected Ion Monitoring Mass Spectral Detection (GC/MS-SIM)

| | |
|---|---|
| 41.00 (DOP, I STD) | 149, 167 and 279 |
| 45.00 (Irganox ®1076) | 219, 515 and 530 |
| Dwell Time: | 100 msec. |

TABLE 5

Instrument Conditions for Gas Chromatography with Total Ion Scanning Mass Spectral Detection (GC/MS)

| | |
|---|---|
| Gas Chromatograph: | HP5890 |
| Detector: | Mass Selective Detector HP5790 |
| Column: | DB-5, 30 mm × 0.25 mm × 0.1 μm (film) |
| Program: | 40° C. for 1 min, 5° C./min to 250° C., 20° C./min to 310° C. held for 25 min. |
| Injection port: | 280° C., with a glass wool plug |
| Transfer Line: | 315° C. |
| Injection volume: | 2 μL, splitless for 30 sec. |
| Mode: | EI+ |
| Scan Range (m/z): | 35–600 |

TABLE 6

Instrument Conditions for Direct Aqueous Injection Gas Chromatography with Flame Ionization Detection (GC/FID)

| | |
|---|---|
| Gas Chromatograph: | HP5890A |
| Detector: | Flame ionization |
| Column: | DB-624 30 m × 0.53 mm × 3.0 μm (film) |
| Program: | 40° C. for 0 min, 15° C./min to 190° C. held for 1 min. |
| Injection port: | 140° C., with a cyclosplitter ® injector liner |
| Detector: | 200° C. |
| Injection volume: | 1 μL, split |
| Data Acquisition System: | Multichrom ® |

TABLE 7

Instrument Conditions for Antioxidant Determination by High Temperature Gas Chromatography with Flame Ionization Detection (GC/FID)

| | |
|---|---|
| Gas Chromatograph: | HP5890A |
| Detector: | Flame ionization |
| Column: | HP-1, Al-Clad, 10 m × 0.53 mm × 0.9 μm (film) |
| Program: | 70° C. for 1 min, 25° C./min to 400° C. held for 5 min. |
| Injection port: | 310° C. |
| Detector: | 400° C. |
| Injection volume: | 1 μL, splitless for 0.5 min. |
| Data Acquisition System: | Multichrom ® |

TABLE 8

Instrument Conditions for Gel Permeation
Chromatography with Ultraviolet (UV) and
Refractive Index (RI) Detection

| | |
|---|---|
| HPLC Pump: | Applied Biosystems, Model 400 |
| Injector: | Rheodyne, Model 7125 |
| UV Detector: | Spectraflow, Model 757 at 254 nm, filter rise time 1 sec |
| RI Detector: | Erma Model ERC-7510 at 30° C., Polarity (+) |
| Data System: | Multichrom |
| Mobile Phase: | Tetrahydrofuran |
| Flow Rate: | 0.7 mL/min. |
| Injection volume: | 20 µL |
| Guard Column: | TosoHaas TSK-GEL ® $H_{XL}$, 4 cm × 6 mm I.D. |
| Analytical column, (in series): | 1) TosoHaas TSK-GEL ® $G3000H_{XL}$, 30 cm × 7.8 mm I.D.<br>2) TosoHaas TSK-GEL ® $G2500H_{XL}$, 30 cm × 7.8 mm I.D. |
| Column Temperature: | 30° C. |

It should be understood that various changes and modifications to the preferred embodiments described herein will be apparent to those skilled in the art. Such changes and modifications can be made without departing from the spirit and scope of the present invention and without diminishing its attendant advantages. It is, therefore, intended that such changes and modifications be covered by the appended claims.

We claim:

1. The method for providing nutrition to patient comprising the steps of:
   providing a container having a first chamber and a second chamber, the first chamber containing lipids, a first peelable seal separating the first chamber from the second chamber, the lipid having a concentration of 2,6-di-t-butyl-4-methyl-phenol of less than 0.050 µg/ml after the container has been autoclaved at 121° C. and allowed to stand for 48 hours at ambient temperature;
   mixing the contents of the container; and
   administering the resultant liquid to the patient.

2. A method for providing nutrition to a patient comprising the steps of:
   providing a container having a first chamber and a second chamber, the first chamber containing lipids, a first peelable seal separating the first chamber from the second chamber, the lipid having a concentration of 2,6-di-t-butyl-4-ethylphenol of less than 0.011 µg/ml after the container has been autoclaved at 121° C. and allowed to stand for 48 hours at ambient temperature;
   mixing the contents of the container; and
   administering the resultant liquid to the patient.

3. A method for providing nutrition to a patient comprising the steps of:
   providing a container having a first chamber and a second chamber, the first chamber containing lipids, a first peelable seal separating the first chamber from the second chamber, the lipid having a concentration of 25-crown-5 ether of less than 0.01 µg/ml after the container has been autoclaved at 121° C. and allowed to stand for 48 hours at ambient temperature;
   mixing the contents of the container; and
   administering the resultant liquid to the patient.

4. A method for providing nutrition to a patient comprising the steps of:
   providing a container having a first chamber and a second chamber, the first chamber containing lipids, a first peelable seal separating the first chamber from the second chamber, the lipid having a concentration of aluminum of less than 0.023 µg/ml after the container has been autoclaved at 121° C. and allowed to stand for 48 hours at ambient temperature;
   mixing the contents of the container; and
   administering the resultant liquid to the patient.

5. A method for providing nutrition to a patient comprising the steps of:
   providing a container having a first chamber and a second chamber, the first chamber containing lipids, a first peelable seal separating the first chamber from the second chamber, the lipid having a concentration of oligomeric propylene of less than 5.6 µg/ml after the container has been autoclaved at 121° C. and allowed to stand for 48 hours at ambient temperature;
   mixing the contents of the container; and
   administering the resultant liquid to the patient.

6. A method for providing nutrition to a patient comprising the steps of:
   providing a container having a first chamber and a second chamber, the first chamber containing lipids, a first peelable seal separating the first chamber from the second chamber, the lipid having a concentration of oligomeric ethylene vinyl acetate of less than 5.6 µg/ml after the container has been autoclaved at 121° C. and allowed to stand for 48 hours at ambient temperature;
   mixing the contents of the container; and
   administering the resultant liquid to the patient.

* * * * *